(12) United States Patent
Knodel

(10) Patent No.: US 8,356,740 B1
(45) Date of Patent: Jan. 22, 2013

(54) CONTROLLING COMPRESSION APPLIED TO TISSUE BY SURGICAL TOOL

(75) Inventor: Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 402 days.

(21) Appl. No.: 12/700,978

(22) Filed: Feb. 5, 2010

Related U.S. Application Data

(60) Provisional application No. 61/209,693, filed on Mar. 9, 2009.

(51) Int. Cl.
*A61B 17/10* (2006.01)

(52) U.S. Cl. .................... 227/175.1; 227/19; 227/181.1

(58) Field of Classification Search ............. 227/175.1, 227/19, 181.1
See application file for complete search history.

(56) References Cited

U.S. PATENT DOCUMENTS

| | | | |
|---|---|---|---|
| 3,581,551 A | 6/1971 | Wilkinson | |
| 3,650,453 A | 3/1972 | Smith, Jr. | |
| 3,899,914 A | 8/1975 | Akiyama | |
| 4,086,926 A | 5/1978 | Green et al. | |
| 4,179,057 A * | 12/1979 | Becht et al. | 227/19 |
| 4,180,196 A * | 12/1979 | Hueil et al. | 227/109 |
| 4,228,895 A | 10/1980 | Larkin | |
| 4,475,679 A | 10/1984 | Fleury, Jr. | |
| 4,633,861 A | 1/1987 | Chow et al. | |
| 4,762,260 A | 8/1988 | Richards et al. | |
| 4,969,591 A | 11/1990 | Richards et al. | |
| 5,156,315 A | 10/1992 | Green et al. | |
| 5,192,288 A | 3/1993 | Thompson et al. | |
| 5,364,001 A * | 11/1994 | Bryan | 227/175.1 |
| 5,413,272 A | 5/1995 | Green et al. | |
| 5,476,206 A | 12/1995 | Green | |
| 5,655,698 A | 8/1997 | Yoon | |
| 5,662,260 A | 9/1997 | Yoon | |
| 5,692,668 A | 12/1997 | Schulze et al. | |
| 5,697,542 A | 12/1997 | Knodel et al. | |
| 5,810,855 A | 9/1998 | Rayburn et al. | |
| 5,816,471 A | 10/1998 | Plyley et al. | |

(Continued)

FOREIGN PATENT DOCUMENTS

EP   1238634   9/1994

(Continued)

OTHER PUBLICATIONS

Gong, Shao W., "Perfectly flexible mechanism and integrated mechanism system design", *Mechanism and Machine Theory 39* (2004), (Nov. 2004),1155-1174.

(Continued)

*Primary Examiner* — Brian D Nash

(57) ABSTRACT

An exemplary surgical apparatus may include a staple holder and an anvil connected to the staple holder, where the anvil includes an anvil body and an anvil plate that floats relative to the anvil body. Another exemplary surgical apparatus may include a staple holder, an anvil connected to the staple holder, and at least one sensor fixed to at least one of the staple holder and the anvil, where at least one sensor is configured to measure stress and/or strain. An exemplary surgical method for treating tissue may include providing an end effector that includes a staple holder and an anvil connected to the staple holder, closing the end effector onto tissue, exerting force on that tissue during closing, and adjusting the gap between the anvil and staple holder during closing along at least a portion of the anvil.

5 Claims, 3 Drawing Sheets

U.S. PATENT DOCUMENTS

| | | | |
|---|---|---|---|
| 5,855,311 A | 1/1999 | Hamblin et al. | |
| 5,865,361 A * | 2/1999 | Milliman et al. | 227/176.1 |
| 5,894,979 A | 4/1999 | Powell | |
| 5,918,791 A | 7/1999 | Sorrentino et al. | |
| 5,964,774 A | 10/1999 | McKean et al. | |
| 6,306,149 B1 | 10/2001 | Meade | |
| 6,602,252 B2 | 8/2003 | Mollenauer | |
| 6,716,232 B1 | 4/2004 | Vidal et al. | |
| 6,817,508 B1 | 11/2004 | Racenet | |
| 6,821,273 B2 | 11/2004 | Mollenauer | |
| 6,843,403 B2 | 1/2005 | Whitman | |
| 7,011,657 B2 | 3/2006 | Truckai et al. | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,140,527 B2 | 11/2006 | Ehrenfels et al. | |
| 7,168,604 B2 | 1/2007 | Milliman et al. | |
| 7,169,146 B2 | 1/2007 | Truckai et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,311,709 B2 | 12/2007 | Truckai et al. | |
| 7,381,209 B2 | 6/2008 | Truckai et al. | |
| 2003/0114851 A1 | 6/2003 | Truckai et al. | |
| 2003/0120284 A1 | 6/2003 | Palacios et al. | |
| 2003/0236551 A1 | 12/2003 | Peterson | |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2006/0273135 A1 * | 12/2006 | Beetel | 227/175.1 |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |
| 2007/0175950 A1 | 8/2007 | Shelton, IV et al. | |
| 2007/0175964 A1 * | 8/2007 | Shelton et al. | 227/180.1 |
| 2008/0078804 A1 * | 4/2008 | Shelton et al. | 227/176.1 |
| 2009/0095790 A1 | 4/2009 | Whitman et al. | |
| 2011/0006103 A1 * | 1/2011 | Laurent et al. | 227/176.1 |

FOREIGN PATENT DOCUMENTS

| | | |
|---|---|---|
| EP | 1464287 | 10/2004 |
| EP | 1736104 | 3/2009 |
| RU | 2080833 | 6/1997 |
| WO | WO-81/01953 | 7/1981 |
| WO | WO-85/01427 | 4/1985 |
| WO | WO 2008/039238 | 4/2008 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology 18*(9), (Nov. 2004),811-817.

Steichen, Felicien M., et al., "Mechanical Sutures in Surgery", *Brit. J. Surg. 60*(3), (Mar. 1973),191-197.

* cited by examiner

CONTROLLING COMPRESSION APPLIED TO TISSUE BY SURGICAL TOOL

This application claims priority to U.S. Provisional Patent Application Ser. No. 61/209,693, filed on Mar. 9, 2009, which is hereby incorporated by reference in its entirety.

FIELD OF THE INVENTION

The invention generally relates to surgical instruments, and more specifically to surgical instruments that clamp tissue.

BACKGROUND

A number of different surgical devices clamp tissue, either as their sole function, or in conjunction with one or more other functions. For example, an endocutter is a surgical tool that staples and cuts tissue to transect that tissue while leaving the cut ends hemostatic. Typically, an endocutter clamps tissue, then staples and transects the clamped tissue. The tissue may be clamped between an anvil and a staple holder of the endocutter. An endocutter is small enough in diameter for use in minimally invasive surgery, where access to a surgical site is obtained through a trocar, port, or small incision in the body. An exemplary endocutter, with true multi-fire capability, is the MICROCUTTER™ brand endocutter proposed by Cardica, Inc. of Redwood City. That device is described in, for example, U.S. Patent Application Publication No. 2009/0065552, published on Mar. 12, 2009 (the "Endocutter Document"). A linear cutter is a larger version of an endocutter, and may be used to transect portions of the gastrointestinal tract. Like an endocutter, a linear cutter also clamps tissue before stapling and transecting it.

The amount of clamping force that is exerted on tissue by a surgical instrument such as an endocutter or linear cutter depends on both the physical configuration of the surgical instrument and the thickness of the tissue to be clamped. As a result, conventional surgical instruments are designed for use with tissue having a particular range of thickness. That range may be narrow, and may be difficult for a surgeon to discern, particularly during minimally-invasive port access and/or robotic surgery.

BRIEF DESCRIPTION OF THE DRAWINGS

The use of the same reference symbols in different figures indicates similar or identical items.

DETAILED DESCRIPTION

Figure 1:
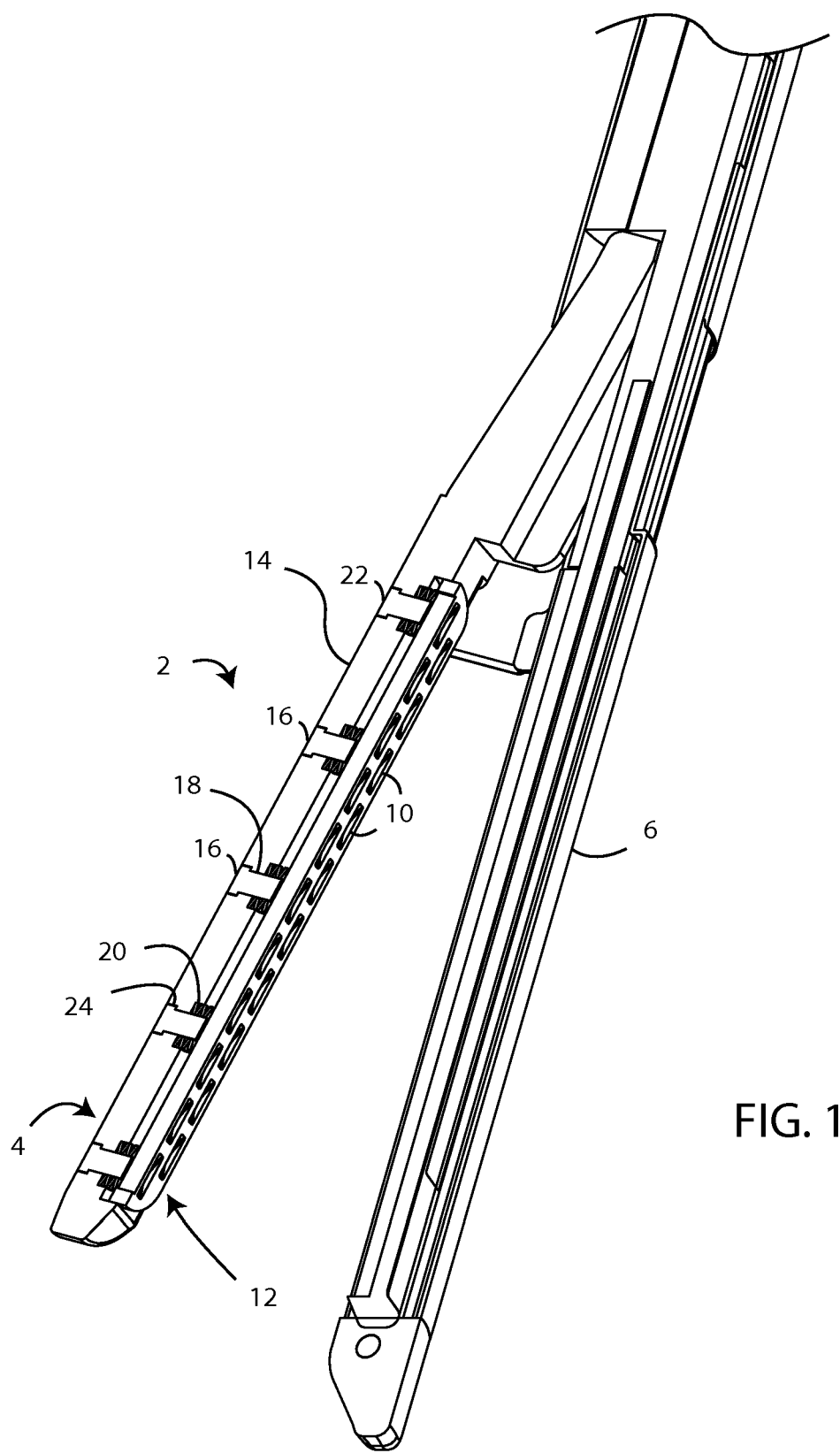
FIG. 1 is a cross-section perspective view of an end effector of a surgical instrument with a staple holder and an anvil, where the anvil plate floats.
Figure 2:
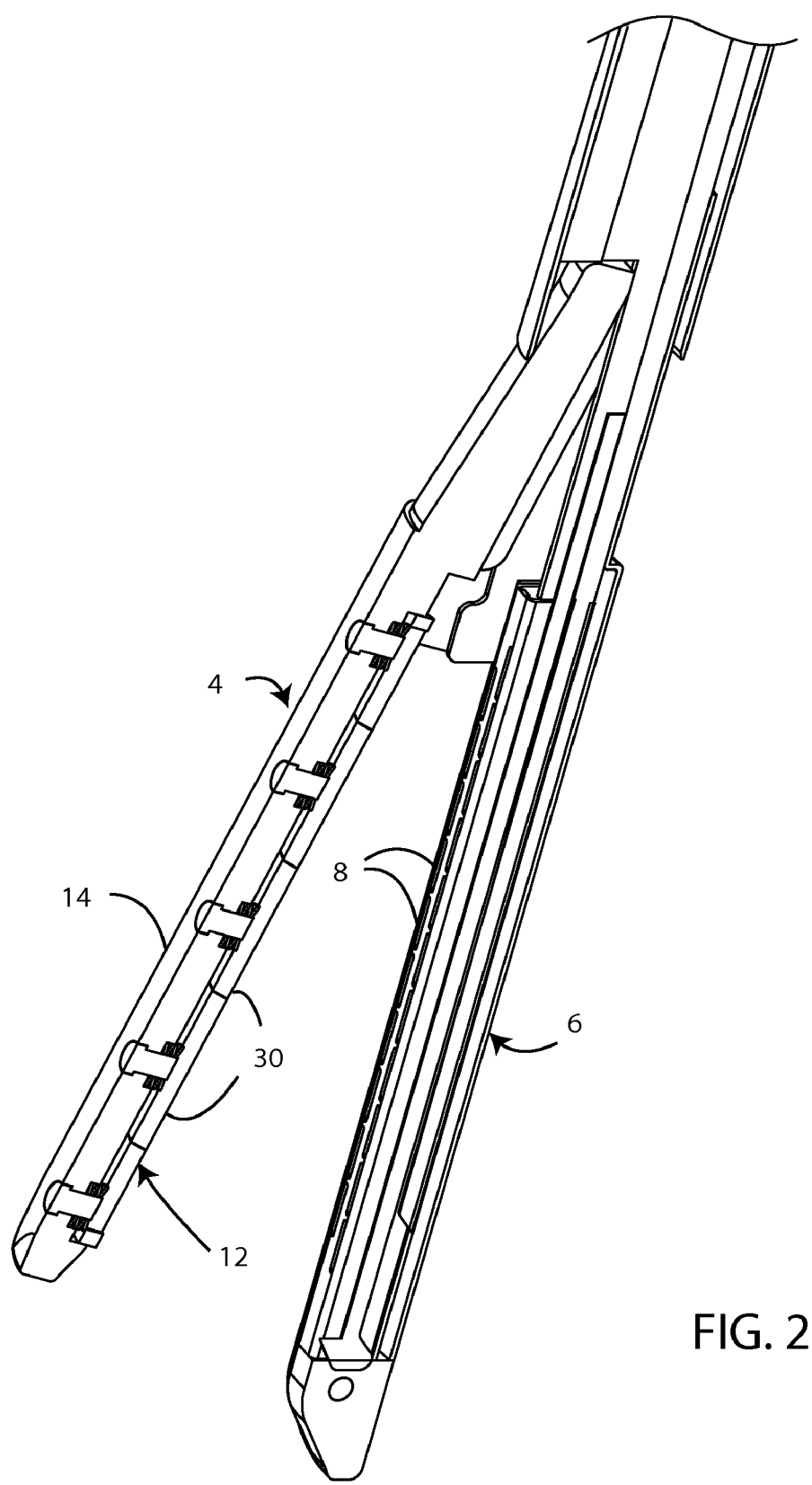
FIG. 2 is a cross-section perspective view of an end effector of a surgical instrument with a staple holder and an anvil, where the anvil plate includes two or more of floating segments.

Referring to FIGS. 1-2, an end effector 2 of a surgical instrument may include an anvil 4 and a staple holder 6. The staple holder 6 may hold one or more staples (not shown) and may be configured for a single use, such that it is fabricated integrally with the remainder of the surgical instrument, or may be configured to hold a detachable cartridge of staples. The staples, and the end effector 2, may be generally as described in U.S. Patent Application Publication No. 2009/0065552, published on Mar. 12, 2009, which is herein incorporated by reference in its entirety. The anvil 4 may be movably connected to the staple holder 6, such as by a pivot, axle, or other joint, such that at least one of the anvil and the staple holder 6 is movable and/or rotatable relative to the other. As in a conventional surgical stapler, the staple holder 6 is configured to deploy staples through apertures 8 in the staple holder 6, toward the anvil 4. The anvil 4 may include staple pockets 10 corresponding to the apertures 8 in the staple holder 6, such that as each staple moves through an aperture 8, that staple encounters a corresponding staple pocket 10 and is deformed by being forced against that staple pocket 10.

The anvil 4 may include an anvil plate 12, in which the staple pocket or pockets 10 are defined. The anvil plate 12 may be oriented toward the staple holder 6. The anvil plate 12 may be connected to the anvil body 14. Advantageously, the anvil plate 12 may float relative to the anvil body 14. The anvil plate 12 may float relative to the anvil body 14 in any suitable manner. The term "float" is expressly defined to mean that the anvil plate 12 is movable relative to the anvil body 14 upon application of a force to the anvil plate 12 over a particular amount. As one example of a floating anvil plate, the anvil plate 12 may include one or more posts 16 that extend into and/or completely through post apertures 18 defined in the anvil body 14. At least one post tunnel 18 may be wider than the corresponding post 16 along at least part of its length, in order to accommodate a spring 20. The post tunnel 18 may be adjacent to the anvil plate 12 such that the spring 20 can exert force directly on the anvil plate 12. The spring 20 may be a coil spring that acts to urge the anvil plate 12 in a direction away from the anvil body 14. The coil spring 20 may be oriented such that the post 16 extends through the center of the coil. Further, at least one post tunnel 18 may include a widened area 24 at the end opposite the anvil plate 12 to accommodate a post button 22 that is wider than a remainder of the post 16. In this way, engagement between the post button 22 and the widened area 24 of the post tunnel 18 establishes a limit for travel of the anvil plate 12 as a result of the spring force applied to the anvil plate 12 by the spring or springs 20. That is, at least one spring 20 may still store energy therein when the post button 22 of at least one post 16 encounters, and is prevented from further motion toward the staple holder 6 by, the widened area 24 of the corresponding post tunnel 18.

The end effector 2 may be moved from an open configuration to a closed configuration, generally as set forth in U.S. Patent Application Publication No. 2009/0065552. The end effector 2 is initially in the open configuration shown in FIGS. 1-2. The end effector 2 is then moved such that tissue to be treated is positioned between the anvil 4 and the staple holder 6. As the end effector 2 closes, the anvil 4 moves closer to the staple holder 6. Alternately, the staple holder 6 moves closer to the anvil 4, or both move closer to one another. Regardless of the particular mode of closing, the anvil plate 12 and staple holder 6 move closer to one another, and as they do so, the tissue held between the anvil 4 and the staple holder 6 begins to be compressed between the anvil plate 12 and the staple holder 6. As the anvil plate 12 and staple holder 6 continue to close, compressive force is exerted on the tissue between the anvil plate 12 and staple holder 6, and that compressive force increases as the end effector 2 closes. After the compressive force reaches a threshold defined by the spring or springs 20, additional closure of the end effector 2 no longer exerts a substantially increased compressive force on the tissue between the anvil plate 12 and staple holder 6; instead, the anvil plate 12 moves away from the staple holder 6, overcoming the biasing force exerted by the spring or springs 20. In this way, if tissue is grasped between the anvil plate 12 and staple holder 6 that is thicker than expected, the anvil plate 12 is moved in a direction away from the staple holder 6, increasing the tissue gap between the anvil plate 12 and staple holder 6 when the end effector 2 is in the closed position, after the anvil 4 and staple holder 6 have ceased motion relative to one another. As the anvil plate 12 moves away from the staple holder 6, each post 16 of the anvil plate 12 slides away from the staple holder 6 along the corresponding post tunnel 18 in the anvil body 14, such that the anvil plate 12 floats relative to the anvil body 14. The spring force exerted by the spring or springs 20 determines the amount of force that is exerted on tissue within the end effector 2, such that tissue is clamped to a force, instead of to a fixed gap between the anvil plate 12 and the staple holder 6. The gap between the anvil plate 12 and staple holder 6 expands to accommodate thicker tissue in the closed configuration of the end effector 2. Adjusting the tissue gap between the anvil 4 and staple holder 6 automatically by allowing the anvil plate 12 to float is defined as "passive" adjusting.

As seen in FIG. 1, the anvil plate 12 may be a single, unitary piece extending longitudinally along the anvil body 14. As seen in FIG. 2, as another example, the anvil plate 12 may be formed collectively by two or more independently-floating segments 30. The segments 30 may be substantially independent from one another, such that each segment 30 may float to a different degree, or not at all. For example, the tissue held in the end effector 2 may be particularly thick at a specific longitudinal location along the anvil 4. If so, the segment or segments 30 positioned against that thick tissue may float, creating a larger gap between the anvil plate 12 and the staple holder 6 along the length defined by that segment or segments 30. The remaining segment or segments 30 may float to a lesser degree, or not at all. In this way, the tissue gap between the anvil plate 12 and the staple holder 6 may be variable along the length of the staple holder 6.

Figure 3:
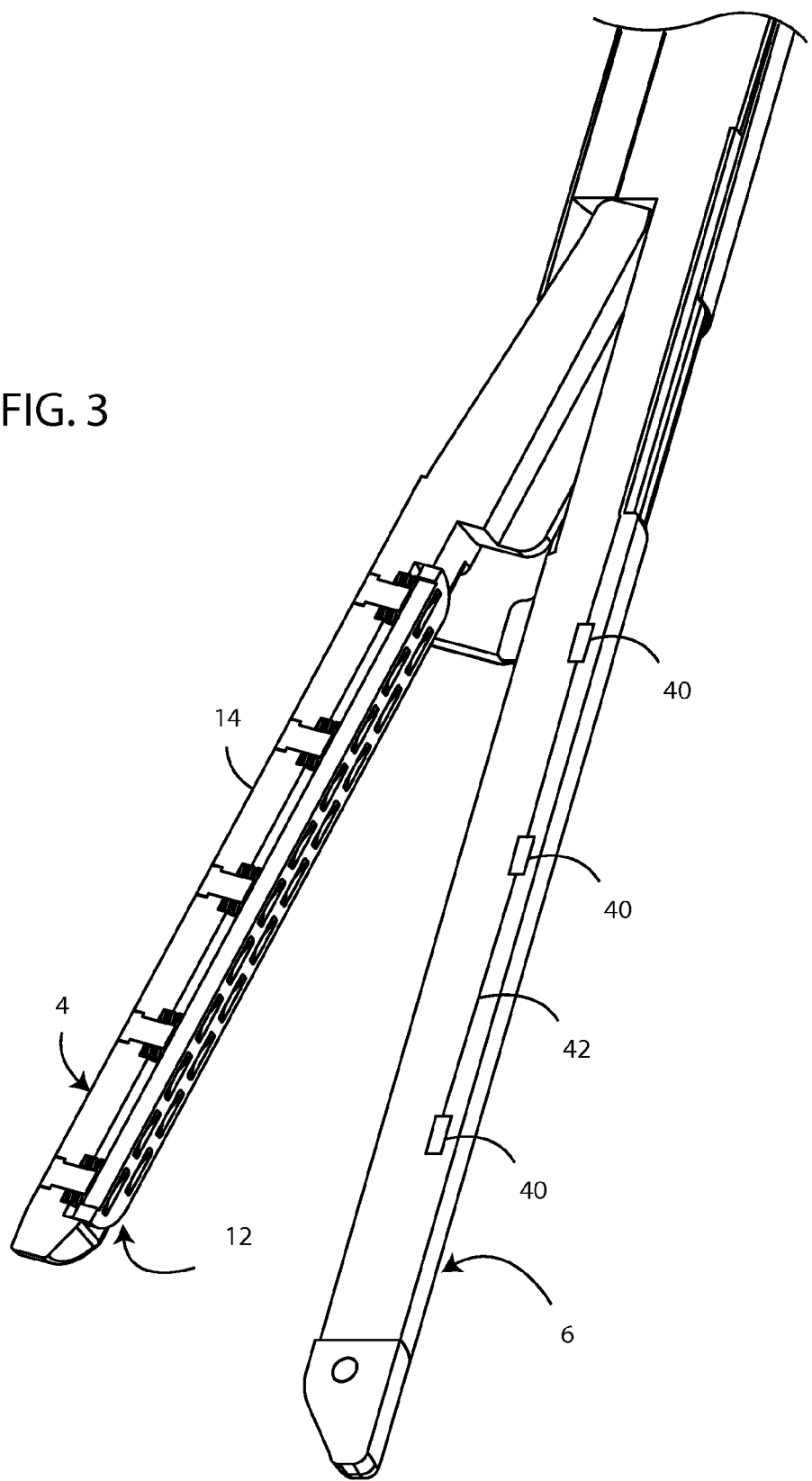
FIG. 3 is a cross-section perspective view of an end effector of a surgical instrument with a staple holder and an anvil, showing sensors attached to the anvil.

Optionally, referring also to FIG. 3, one or more sensors 40 may be fixed on or within the staple holder 6 and/or the anvil 4. During closure of the end effector 2 onto tissue, the anvil 4 and staple holder 6 each experience bending stress in a manner similar to a cantilever beam. The sensors 40 measure that bending stress, and/or the consequent strain, and transmit that data to the user of the tool. Such transmission may be via one or more wires 42 that extend from the end effector 2 to a remainder of the surgical instrument, or wirelessly. The sensors 40 may be strain gauges or any other suitable sensors. The sensors 40 may be powered or unpowered. If they are powered, power may be transmitted to them by one or more cables (not shown), from any suitable power source. By measuring the stress and/or strain in the staple holder 6 and/or anvil 4, and providing that information to the user of the surgical instrument, the user can control the amount of clamping of the end effector 2 to avoid over-clamping the tissue held therein. That is, the operator can begin closing the end effector 2, such that the distance between the anvil 4 and staple holder 6 decreases. As the end effector 2 continues to close, the operator can monitor the level of stress and/or strain, and stop the closure of the end effector 2 at a point where the stress and/or strain in the anvil 4 and/or staple holder 6 reaches or exceeds a particular level that indicates that the anvil 4 and/or staple holder 6 have bent to a particular degree. In this way, the tissue gap between the anvil 4 and staple holder 6 can be maintained within a desired range, such that staples can form against the anvil plate 12 successfully along most or all of the length of the anvil plate 12. Adjusting the tissue gap between the anvil 4 and staple holder 6 manually by monitoring data from the sensor or sensors 40 is defined as "active" adjusting. The sensors 40 may be utilized on a conventional anvil 4 in which the anvil plate 12 does not float, or may be used in conjunction with the floating anvil plate 12 described above and in FIGS. 1-2.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus, comprising:
   a staple holder;
   an anvil connected to said staple holder; said anvil comprising;
   an anvil body; and
   an anvil plate that floats relative to said anvil body; and
   at least one spring configured to urge said anvil plate away from said anvil body.

2. The apparatus of claim 1, wherein said anvil plate includes a plurality of independently-floating segments.

3. The apparatus of claim 1, wherein said anvil plate includes at least one post extending therefrom, and wherein said anvil body includes at least one post tunnel defined therein to receive a corresponding said post.

4. The apparatus of claim 3, further comprising a post button attached to and wider than a corresponding said post, wherein said post button engages said anvil body to limit travel of said anvil plate toward said staple holder.

5. The apparatus of claim 1, wherein said at least one spring comprises a coil spring.

* * * * *